(12) United States Patent
Kraus et al.

(10) Patent No.: US 6,692,479 B2
(45) Date of Patent: Feb. 17, 2004

(54) DONOR BLOOD SAMPLING SYSTEM

(75) Inventors: Menahem Kraus, Rehovot (IL); Eli Shemesh, Ashdod (IL)

(73) Assignee: Teva Medical Ltd., Ashdod (IL)

( * ) Notice: Subject to any disclaimer, the term of this patent is extended or adjusted under 35 U.S.C. 154(b) by 312 days.

(21) Appl. No.: 09/774,283

(22) Filed: Jan. 30, 2001

(65) Prior Publication Data

US 2001/0025167 A1 Sep. 27, 2001

(30) Foreign Application Priority Data

Feb. 14, 2000 (IL) ................................................ 134528

(51) Int. Cl.$^7$ .............................................. A61B 19/00
(52) U.S. Cl. ........................ 604/410; 604/32; 604/403; 604/408
(58) Field of Search ................................ 604/4.01, 6.15, 604/30, 32, 506, 513, 507, 187, 191, 200–206, 218, 232, 264, 533–539, 288.02, 290, 540–544, 317, 319, 403, 408, 410–416

(56) References Cited

U.S. PATENT DOCUMENTS

| | | | |
|---|---|---|---|
| 3,344,785 A | 10/1967 | Hamilton | |
| 3,467,095 A | 9/1969 | Ross | |
| 3,654,924 A | 4/1972 | Wilson et al. | |
| 3,841,835 A | 10/1974 | Kishimoto et al. | ....... 23/253 R |
| 3,877,465 A | 4/1975 | Miyake | |
| 4,219,021 A | 8/1980 | Fink | |
| 4,266,543 A | 5/1981 | Blum | ............... 128/218 N |
| 4,774,964 A | 10/1988 | Bonaldo | |
| 4,843,017 A | 6/1989 | Oberhardt et al. | .......... 436/177 |
| 4,935,012 A | * 6/1990 | Magre et al. | ............... 604/192 |
| 5,084,034 A | 1/1992 | Zanotti | ....................... 604/319 |
| 5,125,414 A | 6/1992 | Dysarz | ....................... 128/763 |

(List continued on next page.)

FOREIGN PATENT DOCUMENTS

| | | |
|---|---|---|
| EP | 0329660 | 8/1989 |
| IL | 101680 | 8/1995 |
| WO | 88/01846 | 3/1988 |
| WO | WO 91/00115 | 1/1991 |
| WO | WO 97/45714 | 12/1997 |
| WO | WO 00/24313 | 5/2000 |

OTHER PUBLICATIONS

SampLink™, TEVA Medical Ltd., Product Information, pp. 1–2, 2001.

Maco Pharma, Exhibitor List, http://www.aabb.org/Professionals . . . , San Antonio, Texas, Oct. 2001, p. 1.

Becton Dickinson—Vacutainer—Venous Blood Collection, "BD Pronto™ Needle Holder", www.bd.com/ca/vacutainer, pp. 1–2, 1997.

Primary Examiner—Glenn K. Dawson
(74) Attorney, Agent, or Firm—Ladas and Parry (57) ABSTRACT

This invention discloses a donor blood sampling apparatus attached to a tubing branch, a donor needle attached to an upstream tube, the donor needle being adapted for drawing blood from a body and a main collection bag attached to a donor tube, characterized by a flow controller. The flow controller includes an inlet flow member including an inlet port connected to the upstream tube and an outlet flow member connected to the inlet flow member and including a first outlet port connected to the tubing branch, and a second outlet port connected to the donor tube, the flow controller having a first position and a second position, wherein in the first position, blood can flow to the sampling apparatus via the first outlet port and the tubing branch, the second outlet port and the donor tube being substantially sealed from blood flowing therein, and wherein in the second position, blood can flow to the main collection bag via the second outlet port and the donor tube, the first outlet port and the tubing branch being substantially sealed from blood flowing therein.

7 Claims, 6 Drawing Sheets

U.S. PATENT DOCUMENTS

| | | | |
|---|---|---|---|
| 5,360,012 A | 11/1994 | Ebara et al. | 128/764 |
| 5,372,143 A | 12/1994 | Bernes et al. | |
| 5,429,612 A * | 7/1995 | Berthier | 604/198 |
| 5,456,678 A | 10/1995 | Nicoletti | 604/413 |
| 5,620,008 A | 4/1997 | Shinar et al. | |
| 5,658,271 A * | 8/1997 | Loubser | 604/410 |
| 5,702,383 A | 12/1997 | Giesler et al. | 604/409 |
| 5,928,166 A | 7/1999 | Shemesh et al. | 600/576 |
| 6,123,859 A * | 9/2000 | Lee et al. | 210/767 |
| 6,126,618 A | 10/2000 | Bischof | 600/576 |
| 6,193,675 B1 | 2/2001 | Kraus et al. | 600/576 |

\* cited by examiner

DONOR BLOOD SAMPLING SYSTEM

FIELD OF THE INVENTION

The present invention relates generally to a donor blood sampling system.

BACKGROUND OF THE INVENTION

It is known that approximately 0.1–0.3% of donated blood units are bacterially contaminated. Although this percentage is much higher than blood contaminated by viruses, such as HIV, nevertheless no routine test is currently performed to detect bacterial contamination. This poses a serious problem because a severely contaminated blood unit can cause sepsis in a recipient.

In general, blood is sampled from the vein for viral contamination-testing and typing after completion of donation. However, it is generally believed that the bacterial contamination stems from skin-embedded bacteria inaccessible to the sanitizing agents normally used before venipuncture. Therefore, systems have already been proposed in the prior art wherein a first volume of blood, typically in the order of 25–50 ml, is sampled to determine blood type and to detect for the presence of viruses. The sampling volume washes away most of the bacterial contamination before the blood is collected in the donor bag. Such a system should satisfy the following criteria:

1. The sampled blood should not be anticoagulated.
2. The collected blood must be anticoagulated.
3. Neither the donor nor collected blood should be exposed to the atmosphere during sampling.
4. The system should be simple and user friendly.

Figure 1:
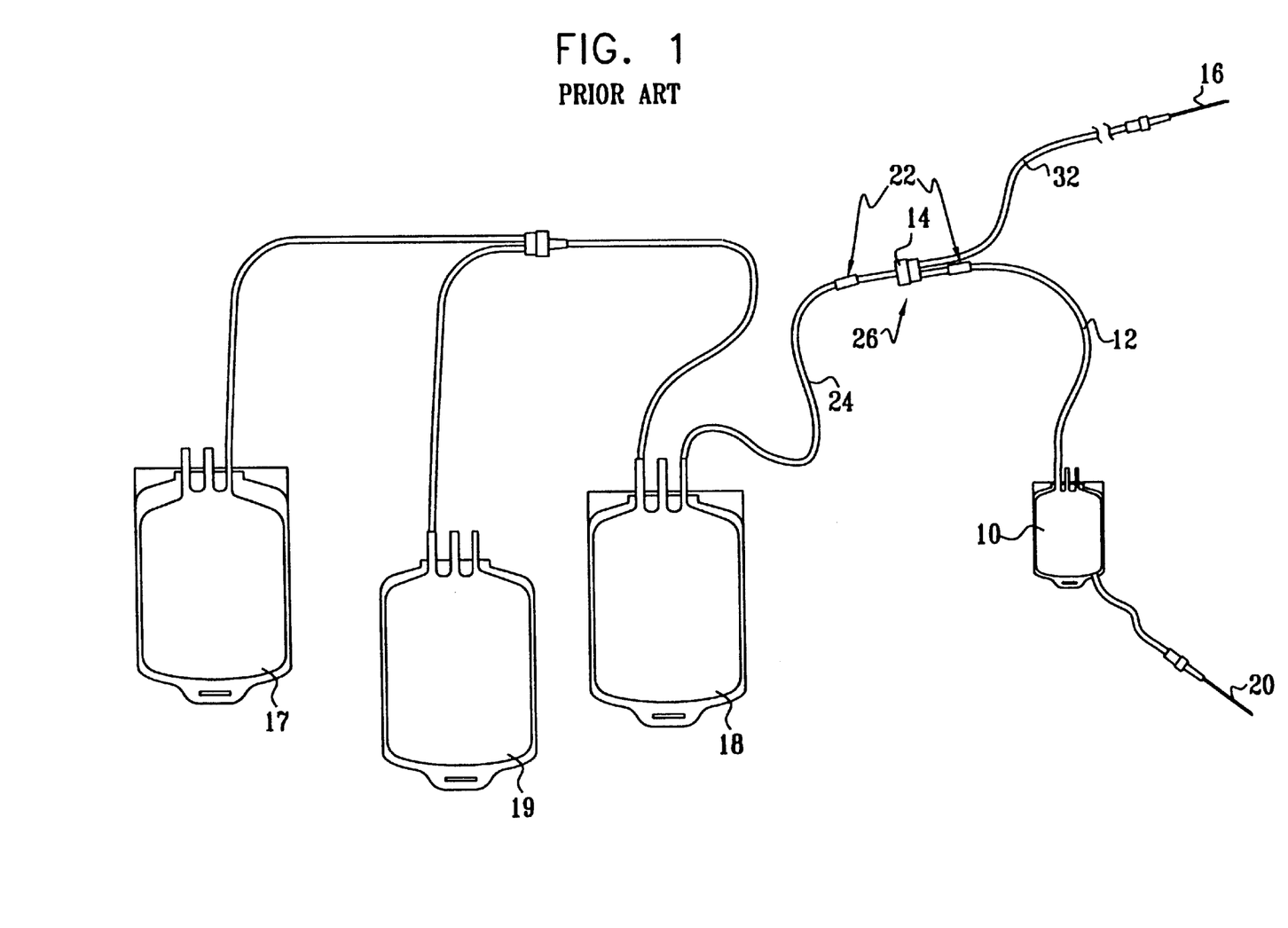
FIG. 1 is a simplified pictorial illustration of a donor blood sampling system of the prior art.

FIG. 1 illustrates a prior art predonation system, commercially available from NPBI, Netherlands. This system includes a small sampling bag 10 (with a volume of 30–50 ml) attached to a tubing branch 12 connected via a Y-connector 14 between a donor needle 16, attached to an upstream tube 32, and a main collection bag 18. Satellite bags 17 and 19 may be connected to bag 18 for processing the blood after collection. A needle 20 is attached to the distal side of sampling bag 10 through which blood is withdrawn while the rest of the system is isolated therefrom by means of external clamps 22 on tubing branch 12 and a donor tube 24 leading to main collection bag 18.

As stated above, the sampled blood should not be anticoagulated, whereas the collected blood must be anticoagulated. Accordingly, an anticoagulant used in collection bag 18 must be prevented from entering sampling bag 10. This means that tubing branch 12 must be sealed at all times before donation. This is achieved by means of a breakaway cannula 26 which is an externally openable closure in tubing branch 12 leading to sampling bag 10.

In the prior art system, the following steps are performed:
1. Clamp donor tube 24.
2. Break breakaway cannula 26.
3. Perform venipuncture and collect first blood in sampling bag 10.
4. Clamp tubing branch 12.
5. Open donor tube clamp 22.
6. Collect blood in main bag 18.
7. Connect a vacuum tube holder to needle 20.
8. Sample blood from sampling bag 10.

Another prior art system that operates in a similar manner is commercially available from Macopharma, France. Although the prior art systems approximately satisfy the four criteria mentioned hereinabove, nevertheless, they are labor intensive and cumbersome.

SUMMARY OF THE INVENTION

The present invention seeks to provide a simple, inexpensive and very easy-to-use donor blood sampling system which solves the abovementioned problems of the prior art.

In contrast to the prior art, in the present invention, the donor tube and tubing branch are preferably connected to the tube leading to the donor needle via a unique flow controller. The flow controller provides simple, straightforward blood flow control. The flow controller has only two operating positions. In a first position, this being the position in which the system is provided to the end-user, blood can flow to the sampling bag via the tubing branch, and the donor tube is substantially sealed from blood flowing therein. A user can place the flow controller into a second position, wherein blood can flow to the main collection bag via the donor tube, and the tubing branch is substantially sealed from blood flowing therein. In the present invention, not one drop of sampled blood flows towards the collection bag and no anticoagulant agent can contaminate the sampling bag. Neither the donor nor collected blood is ever exposed to the atmosphere during sampling. The system is very simple and user friendly.

There is thus provided in accordance with a preferred embodiment of the present invention a donor blood sampling system including sampling apparatus attached to a tubing branch, a donor needle attached to an upstream tube, the donor needle being adapted for drawing blood from a body, and a main collection bag attached to a donor tube, characterized by a flow controller including an inlet flow member including an inlet port connected to the upstream tube, and an outlet flow member connected to the inlet flow member and including a first outlet port connected to the tubing branch, and a second outlet port connected to the donor tube, the flow controller having a first position and a second position, wherein in the first position, blood can flow to the sampling apparatus via the first outlet port and the tubing branch, the second outlet port and the donor tube being substantially sealed from blood flowing therein, and wherein in the second position, blood can flow to the main collection bag via the second outlet port and the donor tube, the first outlet port and the tubing branch being substantially sealed from blood flowing therein.

In accordance with a preferred embodiment of the present invention a seal is positioned between the inlet flow and outlet flow members that substantially seals the outlet ports from each other.

In accordance with a preferred embodiment of the present invention the outlet flow member is arranged for rotation with respect to the inlet flow member between the first and second positions.

Further in accordance with a preferred embodiment of the present invention the inlet flow member includes a rim that extends from the inlet flow member, the rim defining a receiving volume inwards of a perimeter of the rim, and the outlet flow member sealingly and rotatingly sits in the receiving volume.

Still further in accordance with a preferred embodiment of the present invention the outlet ports are positioned generally symmetrically about a central axis of the flow controller and the inlet port is positioned offset from the central axis.

Additionally in accordance with a preferred embodiment of the present invention the seal includes an inner seal connected to an outer seal, wherein a central axis of the inner seal is offset from a central axis of the outer seal.

Still further in accordance with a preferred embodiment of the present invention the seal sits in a groove formed in the inlet flow member.

In accordance with a preferred embodiment of the present invention the seal is formed with a channel having two branches arranged for fluid communication with the inlet port and the outlet ports, wherein when one of the branches is in fluid communication with the inlet port and one of the outlet ports, the other branch is not in fluid communication with the other outlet port, thereby substantially preventing fluid flow to the other outlet port.

Further in accordance with a preferred embodiment of the present invention a volume-limiting clamp is clamped to the sampling bag.

In accordance with a preferred embodiment of the present invention the sampling apparatus includes a sampling bag.

In accordance with another preferred embodiment of the present invention the sampling apparatus includes a sampling device that clamps on the tubing branch and is operative to divert blood into a collection tube.

Further in accordance with a preferred embodiment of the present invention the flow controller includes a base formed with a pivot edge and pockets for receiving therein the tubing branch and the donor tube, and a lever pivotedly attached to the base about the pivot edge, the lever including a pair of protrusions that are arranged to press against and substantially seal one of the tubing branch and the donor tube.

Still further in accordance with a preferred embodiment of the present invention the lever includes a pair of lips adapted to fixedly snap onto ridges protruding from the base.

BRIEF DESCRIPTION OF THE DRAWINGS

The present invention will be understood and appreciated more fully from the following detailed description, taken in conjunction with the drawings in which.

DETAILED DESCRIPTION OF A PREFERRED EMBODIMENT

Figure 2:
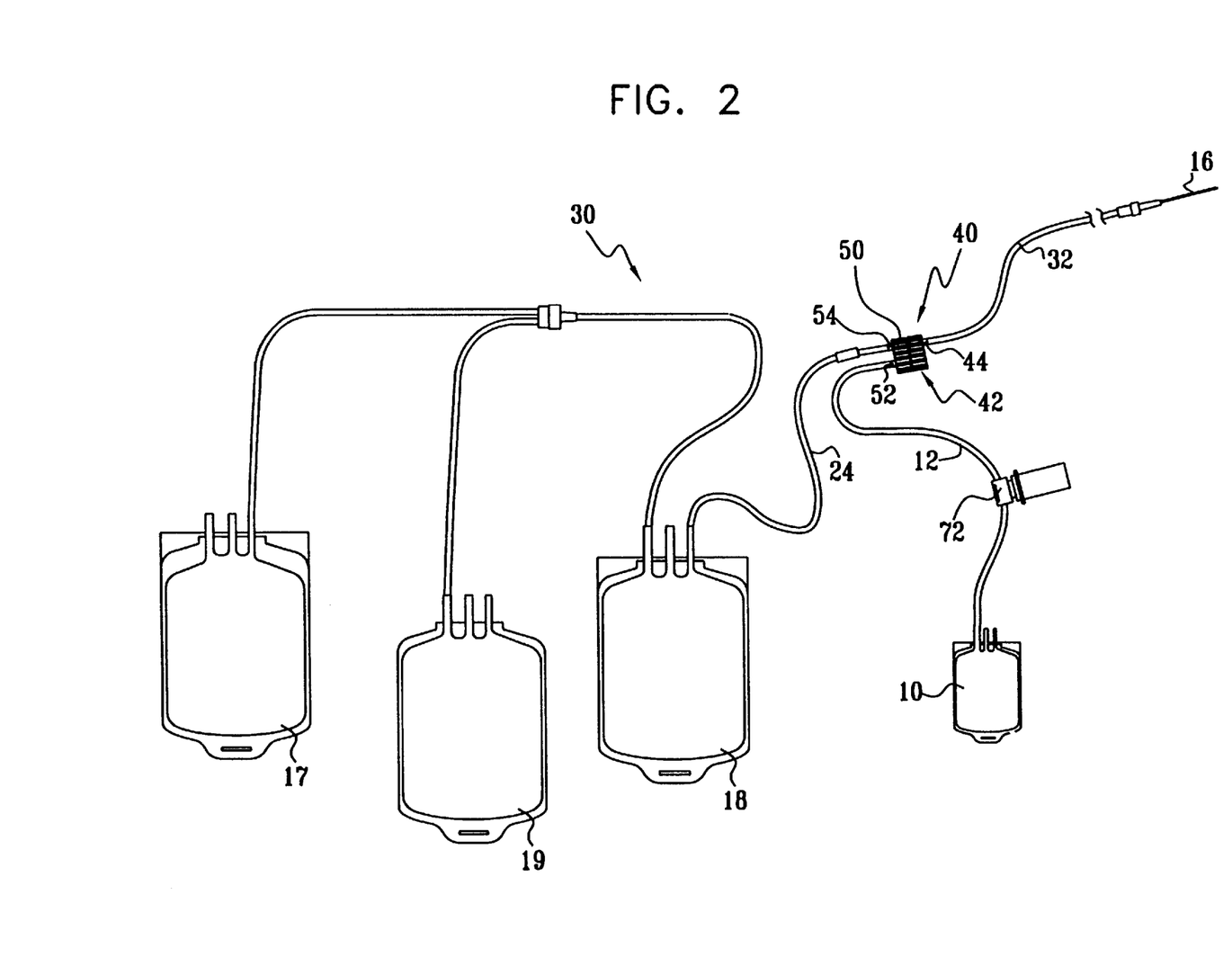
FIG. 2 is a simplified pictorial illustration of a donor blood sampling system constructed and operative in accordance with a preferred embodiment of the present invention.

Reference is now made to FIG. 2 which illustrates a donor blood sampling system 30 constructed and operative in accordance with a preferred embodiment of the present invention. As in the prior art system described hereinabove, system 30 preferably includes a small sampling bag 10 attached to a tubing branch 12, a donor needle 16 attached to an upstream tube 32, and a main collection bag 18 attached to a donor tube 24. Satellite bags 17 and 19 may also be provided.

In contrast to the prior art, in system 30, donor tube 24 and tubing branch 12 are preferably connected to tube 32 via a flow controller 40. Flow controller 40 provides simple, straightforward blood flow control. Flow controller 40 has only two operating positions. In a first position, this being the position in which system 30 is provided to the end-user, blood can flow to sampling bag 10 via tubing branch 12, and donor tube 24 is substantially sealed from blood flowing therein. A user can place flow controller 40 into a second position, wherein blood can flow to bag 18 via donor tube 24, and tubing branch 12 is substantially sealed from blood flowing therein, as described in detail hereinbelow.

Figures 3, 4, 5:
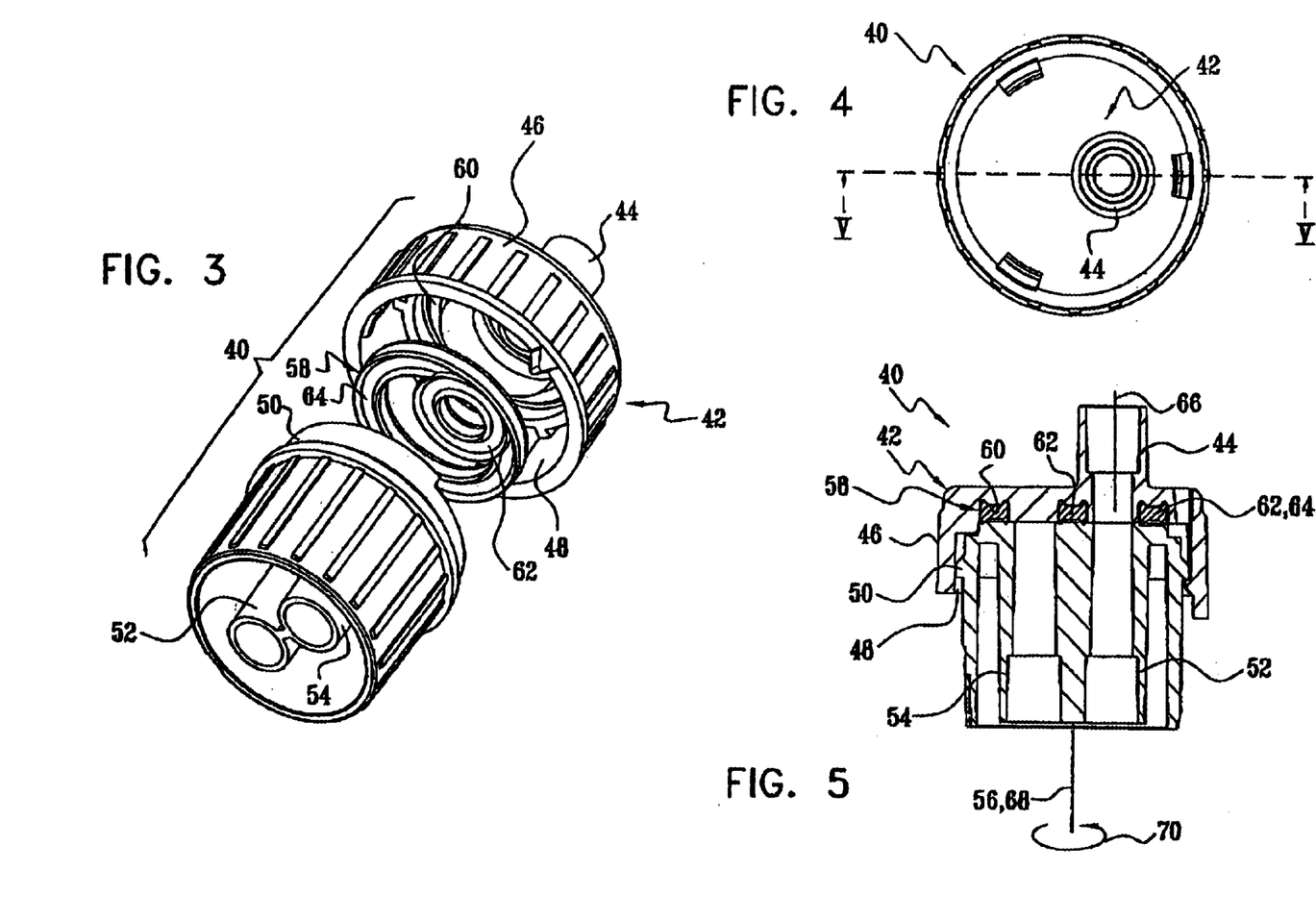
FIG. 3 is a simplified pictorial, exploded illustration of a flow controller used in the donor blood sampling system of FIG. 2, constructed and operative in accordance with a preferred embodiment of the present invention.
FIGS. 4 and 5 are simplified top-view and sectional illustrations, respectively, of the flow controller of FIG. 3, FIG. 5 being taken along lines V—V in FIG. 4.

Reference is now made to FIGS. 3–5 which illustrate flow controller 40, constructed and operative in accordance with a preferred embodiment of the present invention. Flow controller 40 preferably includes an inlet flow member 42 with an inlet port 44 connected to upstream tube 32 (FIG. 2). Inlet flow member 42 preferably includes a rim 46 that extends therefrom in a direction generally opposite to inlet port 44. A receiving volume 48 is defined inwards of a perimeter of rim 46, in which sealingly and rotatingly sits an outlet flow member 50.

Outlet flow member 50 preferably includes a first outlet port 52 connected to tubing branch 12 (FIG. 2), and a second outlet port 54 connected to donor tube 24 (FIG. 2). Outlet ports 52 and 54 are preferably positioned generally symmetrically about a central axis 56 (FIG. 5) of flow controller 40 and inlet port 44 is preferably positioned offset from the central axis 56. A seal 58 is preferably positioned between inlet and outlet flow members 42 and 50 that substantially seals outlet ports 52 and 54 from each other. In a preferred embodiment, seal 58 sits in a groove 60 formed in inlet flow member 42, and includes an inner seal 62 connected to an outer seal 64. A central axis 66 of inner seal 62 is preferably offset from a central axis 68 of outer seal 64 (FIG. 5), generally the same amount of offset as the offset arrangement of inlet port 44 with respect to axis 56.

Outlet flow member 50 is arranged for rotation about axis 56 with respect to inlet flow member 42 between first and second positions. In the first position, shown in FIG. 5, blood can flow to sampling bag 10 via first outlet port 52 and tubing branch 12, second outlet port 54 and donor tube 24 being substantially sealed from blood flowing therein. Inlet flow member 42 can be rotated about axis 56 with respect to outlet flow member 50, generally in the direction of an arrow 70 (FIG. 5) to a second position. In this position, blood can flow to main collection bag 18 via second outlet port 54 and donor tube 24, first outlet port 52 and tubing branch 12 being substantially sealed from blood flowing therein.

Thus, in the present invention, the steps for sampling and collecting blood are reduced and simplified to the following:
1. Perform venipuncture and commence drawing blood with flow controller 40 in first position. (Blood initially flows to sampling bag 10.)
2. After sampling bag 10 has filled, place flow controller 40 into second position.

3. Collect blood in bag 18.
4. During or after donation, sample blood from sampling bag 10, as is now described with reference to FIG. 2.

Referring to FIG. 2, in a most preferred embodiment, a sampling device 72 is attached to tubing branch 12 upstream of sampling bag 10. Sampling device 72 is preferably constructed in accordance with the device described in published PCT patent application WO 97/45714, assigned to the present assignee, the disclosure of which is incorporated herein by reference. Sampling device 72 clamps conveniently and easily on tubing branch 12 and allows sampling blood from tubing branch 12 into a collection tube, e.g., a vacuum tube, such as a familiar VACUTAINER tube. Sampling bag 10 needs no special attachments. It is further noted that sampling device 72 can be used to sample blood without any sampling bag 10, the blood being diverted into the vacuum tube.

Figure 6:
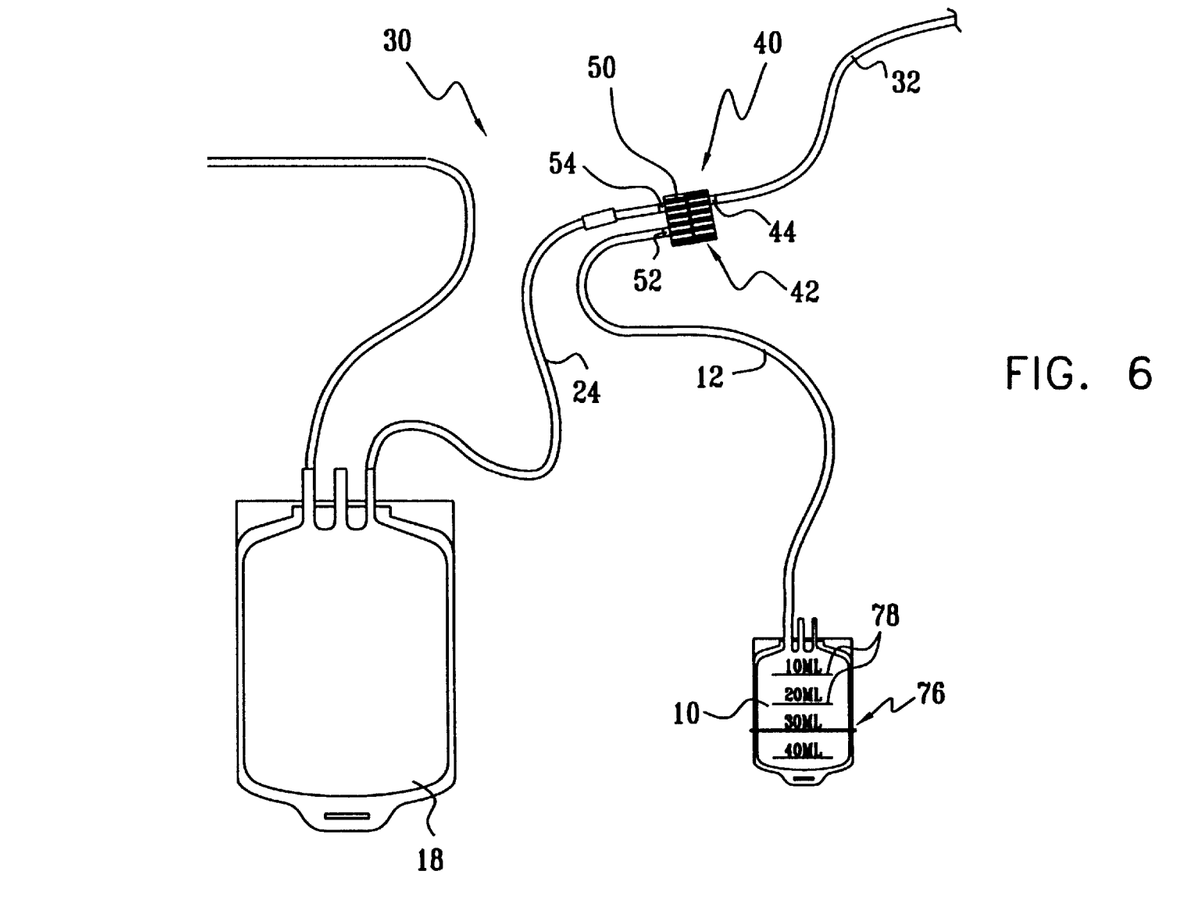
FIG. 6 is a simplified pictorial illustration of the donor blood sampling system of FIG. 2, with a volume-limiting clamp on a sampling bag, in accordance with a preferred embodiment of the present invention.

Referring to FIG. 6, it is seen that sampling bag 10 may be provided with a volume-limiting clamp 76 that limits the amount of blood collected in sampling bag 10. Sampling bag 10 may be provided with graduations 78 to indicate a position for placing clamp 76.

Reference is now made to FIGS. 7, 8, 9 and 10 which are simplified pictorial illustrations of flow controllers, constructed and operative in accordance with four different preferred embodiments of the present invention, wherein a seal 80 is arranged for rotation with respect to inlet and outlet flow members 82 and 84 of a flow controller between first and second positions. Outlet flow member 84 comprises a first outlet port 86 and a second outlet port 88.

Seal 80 is preferably formed with a channel 90 having two branches 92 and 94 arranged for fluid communication with inlet port 82 and outlet ports 86 and 88, wherein when one of the branches is in fluid communication with inlet port 82 and one of the outlet ports (86 or 88), the other branch is not in fluid communication with the other outlet port, thereby substantially preventing fluid flow to the other outlet port, as is now described in more detail.

Figure 7:
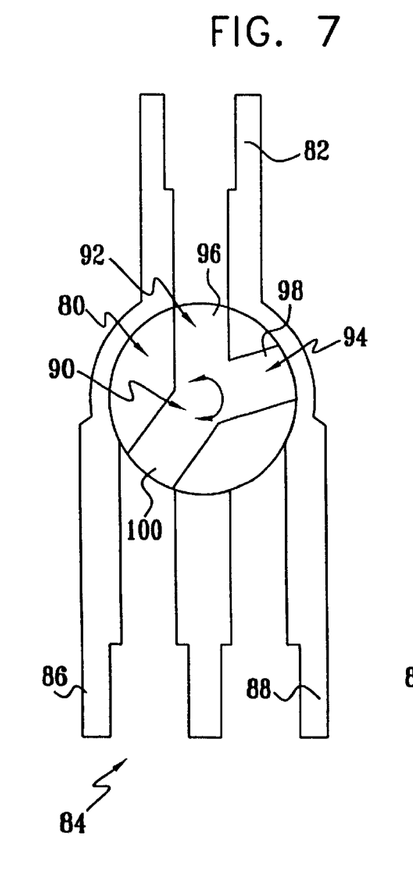
FIGS. 7, 8, 9 and 10 are simplified pictorial illustrations of flow controllers useful in the system of FIG. 2, constructed and operative in accordance with four different preferred embodiments of the present invention, wherein a seal is arranged for rotation with respect to inlet and outlet flow members of a flow controller between first and second positions.

In the embodiment of FIG. 7, the branches 92 and 94 together form a Y-shaped channel 90, with upper members 96 and 98 each extending into a lower member 100. In other words, branch 92 comprises flow from upper member 96 to lower member 100, and branch 94 comprises flow from upper member 98 to lower member 100.

Figure 8:
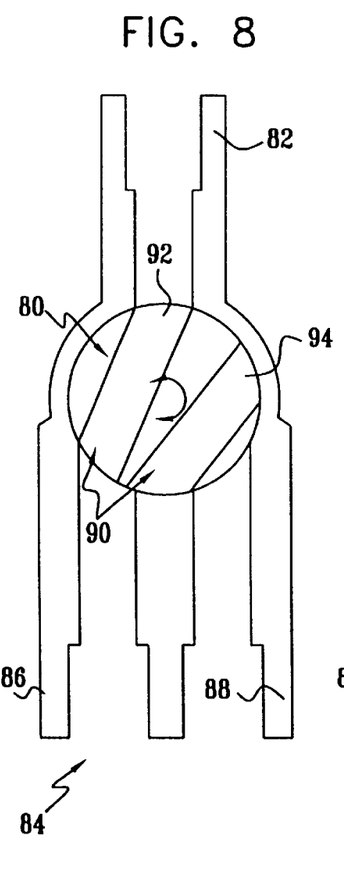

In the embodiment of FIG. 8, branches 92 and 94 are two separate, generally linear branches.

Figure 9:
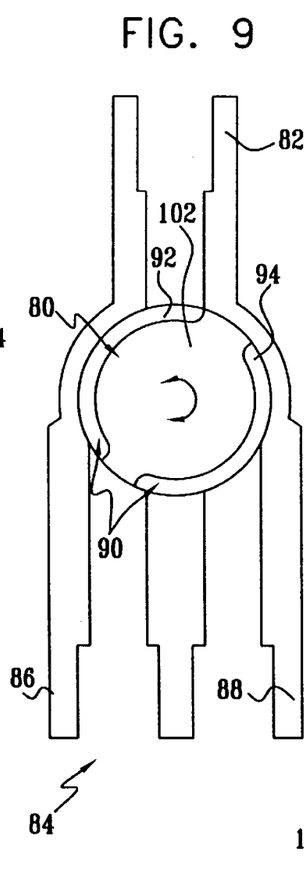

In the embodiment of FIG. 9, branches 92 and 94 are two separate, generally arcuate branches cut out on the perimeter of a disc 102.

Figures 10, 11:
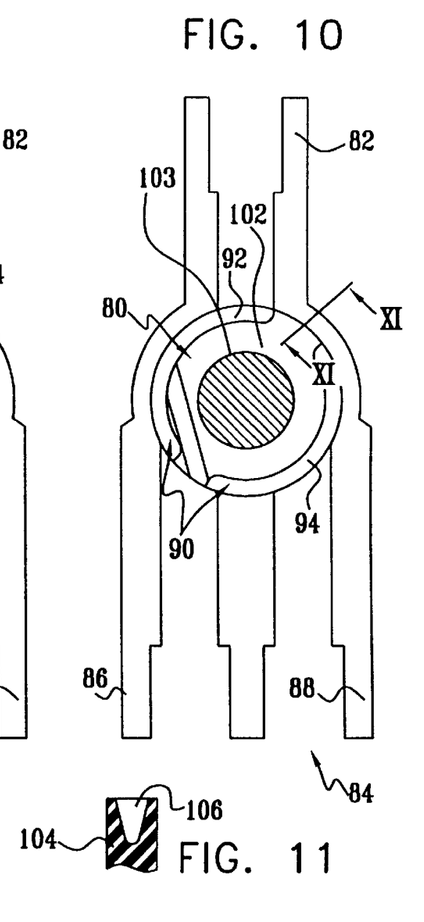
FIG. 11 is a simplified sectional illustration of a portion of the seal of the embodiment of FIG. 10, taken along lines XI—XI in FIG. 10.

In the embodiment of FIG. 10, which is basically the same as that of FIG. 9, disc 102 is mounted on a central axle 103. Disc 102 is preferably formed with a cross section shaped like a trough 106, as seen in the sectional view of FIG. 11. Disc 102 is preferably formed of an elastomer. In all of the embodiments of FIGS. 7–10, seal 80 rotates generally about its center point.

Figure 12:
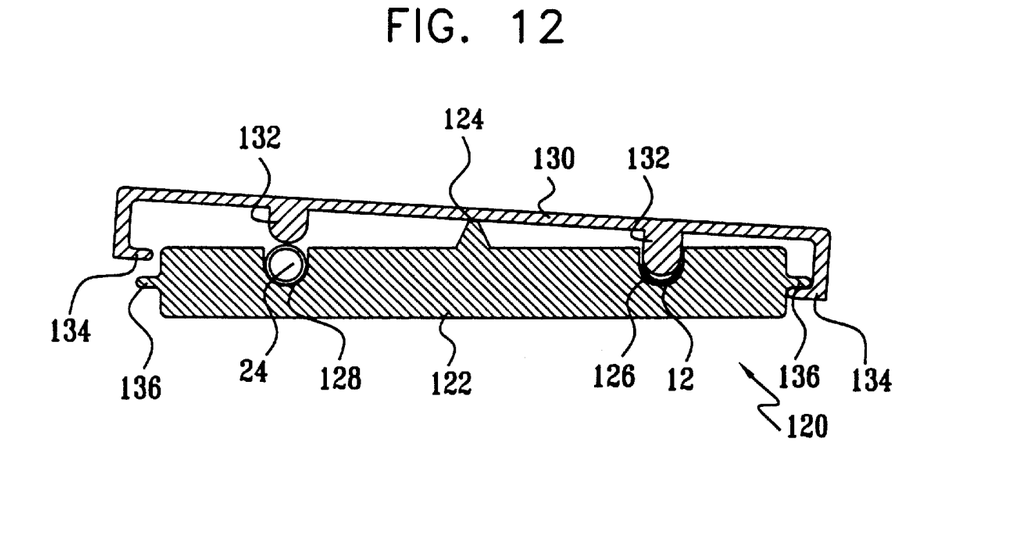
FIGS. 12 and 13 are simplified sectional and top-view illustrations of a flow controller useful in the donor blood sampling system of FIG. 2, constructed and operative in accordance with yet another preferred embodiment of the present invention.
Figure 13:
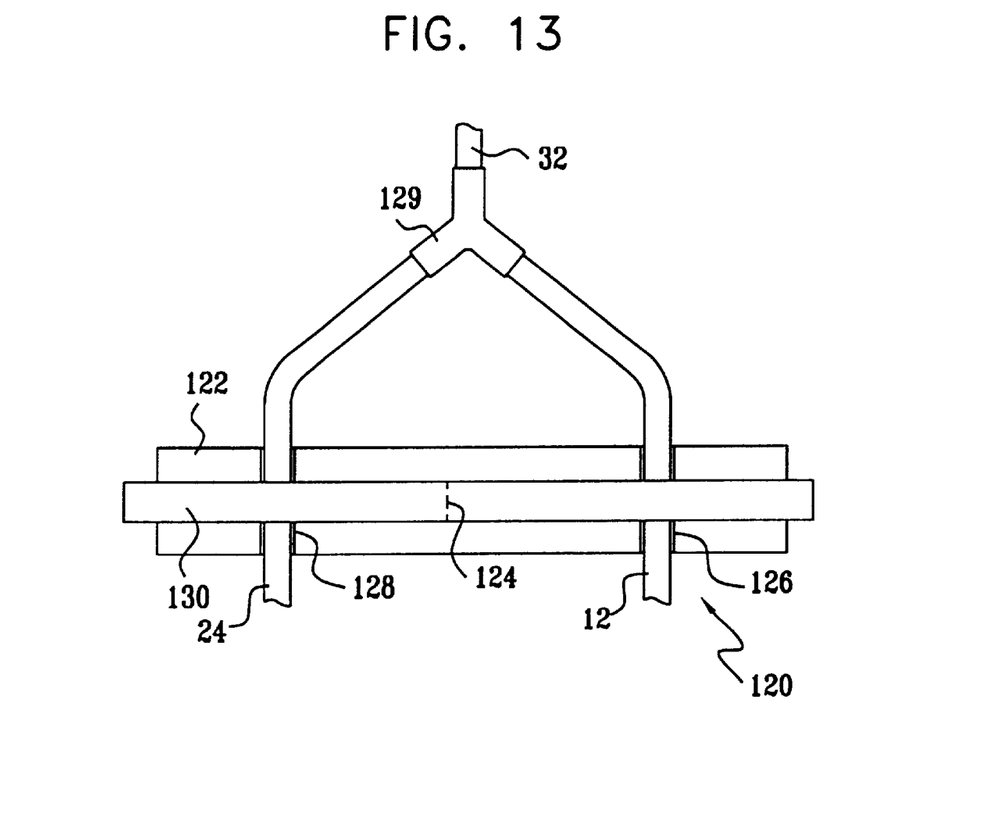

Reference is now made to FIG. 12 which illustrates a flow controller 120 useful in the donor blood sampling system of FIG. 2, constructed and operative in accordance with yet another preferred embodiment of the present invention. Elements common to flow controllers 40 and 120 are designated by the same numerals. Flow controller 120 preferably includes a base 122 formed with a pivot edge 124. Base 122 is preferably formed with pockets 126 and 128 for receiving therein tubing branch 12 and donor tube 24, respectively. A branched connector 129 (FIG. 13) is preferably provided for connecting upstream tube 32 to tubing branch 12 and donor tube 24.

A lever 130 is preferably pivotedly attached to base 122 about pivot edge 124. Lever 130 preferably includes a pair of protrusions 132 that are arranged to press against and substantially seal either tubing branch 12 or donor tube 24. In FIG. 12, it is seen that one of the protrusions 132 presses against and substantially seals tubing branch 12, while the other protrusion 132 does not seal donor tube 24, thereby allowing blood flow through donor tube 24. Lever 130 may be provided with a pair of lips 134 that can fixedly snap onto ridges 136 protruding from base 122, as shown in FIG. 12.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. A donor blood sampling system comprising:
   sampling apparatus attached to a tubing branch;
   a donor needle attached to an upstream tube, said donor needle being adapted for drawing blood from a body; and
   a main collection bag attached to a donor tube; characterized by
   a flow controller comprising:
   an inlet flow member including an inlet port connected to said upstream tube; and
   an outlet flow member connected to said inlet flow member and comprising a first outlet port connected to said tubing branch, and a second outlet port connected to said donor tube, said flow controller having a first position and a second position, wherein in said first position, blood can flow to said sampling apparatus via said first outlet port and said tubing branch, said second outlet port and said donor tube being substantially sealed from blood flowing therein, and wherein in said second position, blood can flow to said main collection bag via said second outlet port and said donor tube, said first outlet port and said tubing branch being substantially sealed from blood flowing therein, and wherein said outlet flow member is arranged for rotation with respect to said inlet flow member between the first and second positions.

2. A donor blood sampling system comprising:
   sampling apparatus attached to a tubing branch;
   a donor needle attached to an upstream tube, said donor needle being adapted for drawing blood from a body; and
   a main collection bag attached to a donor tube;
   characterized by
   a flow controller comprising:
   an inlet flow member including an inlet port connected to said upstream tube;
   an outlet flow member connected to said inlet flow member and comprising a first outlet port connected to said tubing branch, and a second outlet port connected to said donor tube, said flow controller having a first position and a second position wherein in said first position, blood can flow to said sampling apparatus via said first outlet port and said tubing branch, said second outlet port and said donor tube being substantially sealed from blood flowing therein, and wherein in said second position, blood can flow to said main collection bag via said second outlet port and said donor tube, said first outlet port and said tubing branch being substantially sealed from blood flowing therein, and wherein said outlet flow member is arranged for rotation with respect to said inlet flow member between the first and second positions; and a seal positioned between said inlet flow and outlet flow members that substantially seals said outlet ports from each other.

3. A donor blood sampling system comprising:

sampling apparatus attached to a tubing branch;

a donor needle attached to an upstream tube, said donor needle being adapted for drawing blood from a body; and a main collection bag attached to a donor tube;

characterized by a flow controller comprising:

an inlet flow member including an inlet port connected to said upstream tube; and an outlet flow member connected to said inlet flow member and comprising a first outlet port connected to said tubing branch, and a second outlet port connected to said donor tube, said flow controller having a first position and a second position, wherein in said first position, blood can flow to said sampling apparatus via said first outlet port and said tubing branch, said second outlet port and said donor tube being substantially sealed from blood flowing therein, and wherein in said second position, blood can flow to said main collection bag via said second outlet port and said donor tube, said first outlet port and said tubing branch being substantially sealed from blood flowing therein, said inlet flow member comprising a rim extending in a direction generally opposite said inlet port, said rim defining a receiving volume inwards of a perimeter of said rim, and said outlet flow member sealingly and rotatingly sits in the receiving volume.

4. A donor blood sampling system comprising:

sampling apparatus attached to a tubing branch;

a donor needle attached to an upstream tube, said donor needle being adapted for drawing blood from a body; and a main collection bag attached to a donor tube;

characterized by a flow controller comprising:

an inlet flow member including an inlet port connected to said upstream tube; and an outlet flow member connected to said inlet flow member and comprising a first outlet port connected to said tubing branch, and a second outlet port connected to said donor tube, said flow controller having a first position and a second position, wherein in said first position, blood can flow to said sampling apparatus via said first outlet port and said tubing branch, said second outlet port and said donor tube being substantially sealed from blood flowing therein, and wherein in said second position, blood can flow to said main collection bag via said second outlet port and said donor tube, said first outlet port and said tubing branch being substantially sealed from blood flowing therein, and wherein said outlet ports are positioned generally symmetrically about a central axis of said flow controller and said inlet port is positioned offset from the central axis.

5. A donor blood sampling system comprising:

sampling apparatus attached to a tubing branch;

a donor needle attached to an upstream tube, said donor needle being adapted for drawing blood from a body; and a main collection bag attached to a donor tube;

characterized by a flow controller comprising:

an inlet flow member including an inlet port connected to said upstream tube;

an outlet flow member connected to said inlet flow member and comprising a first outlet port connected to said tubing branch, and a second outlet port connected to said donor tube, said flow controller having a first position and a second position, wherein in said first position, blood can flow to said sampling apparatus via said first outlet port and said tubing branch, said second outlet port and said donor tube being substantially sealed from blood flowing therein, and wherein in said second position, blood can flow to said main collection bag via said second outlet port and said donor tube, said first outlet port and said tubing branch being substantially sealed from blood flowing therein; and a seal positioned between said inlet flow member and said outlet flow member that substantially seals said outlet ports from each other, said seal comprising an inner seal connected to an outer seal, wherein a central axis of said inner seal is offset from a central axis of said outer seal.

6. A donor blood sampling system comprising:

sampling apparatus attached to a tubing branch;

a donor needle attached to an upstream tube, said donor needle being adapted for drawing blood from a body; and a main collection bag attached to a donor tube;

characterized by a flow controller comprising;

an inlet flow member including an inlet port connected to said upstream tube;

an outlet flow member connected to said inlet flow member and comprising a first outlet port connected to said tubing branch, and a second outlet port connected to said donor tube, said flow controller having a first position and a second position, wherein in said first position, blood can flow to said sampling apparatus via said first outlet port and said tubing branch, said second outlet part and said donor tube being substantially sealed from blood flowing therein, and wherein in said second position, blood can flow to said main collection bag via said second outlet port and said donor tube, said first outlet port and said tubing branch being substantially sealed from blood flowing therein; and a seal positioned between said inlet flow member and said outlet flow member that substantially seals said outlet ports from each other, wherein said seal sits in a groove formed in said inlet flow member.

7. A donor blood sampling system comprising:

sampling apparatus attached to a tubing branch;

a donor needle attached to an upstream tube, said donor needle being adapted for drawing blood from a body; and a main collection bag attached to a donor tube;

characterized by a flow controller comprising:

an inlet flow member including an inlet port connected to said upstream tube;

an outlet flow member connected to said inlet flow member and comprising a first outlet port connected to said tubing branch, and a second outlet port connected to said donor tube, said flow controller having a first position and a second position, wherein in said first position, blood can flow to said sampling apparatus via said first outlet port and said tubing branch, said second outlet port and said donor tube being substantially sealed from blood flowing therein, and wherein in said second position, blood can flow to said main collection bag via said second outlet port and said donor tube, said first outlet port and said tubing branch being substantially sealed from blood flowing therein; and a seal positioned between said inlet flow and outlet flow members that substantially seals said outlet ports from each other, wherein said seal is formed with a channel having two branches arranged for fluid communication with said inlet port and said outlet ports, wherein when one of the branches is in fluid communication with said inlet port and one of said outlet ports, the other branch is not in fluid communication with the other outlet port, thereby substantially preventing fluid flow to the other outlet port.

\* \* \* \* \*

UNITED STATES PATENT AND TRADEMARK OFFICE
CERTIFICATE OF CORRECTION

PATENT NO. : 6,692,479 B2  
DATED : February 17, 2004  
INVENTOR(S) : Menahem Kraus et al.

It is certified that error appears in the above-identified patent and that said Letters Patent is hereby corrected as shown below:

<u>Title page,</u>  
Item [*] Notice, "312" should read -- 363 --.

Signed and Sealed this

Twenty-seventh Day of April, 2004

JON W. DUDAS  
*Acting Director of the United States Patent and Trademark Office*